United States Patent
Wojcik

(10) Patent No.: US 7,052,483 B2
(45) Date of Patent: May 30, 2006

(54) TRANSCUTANEOUS INSERTER FOR LOW-PROFILE INFUSION SETS

(75) Inventor: Steven Wojcik, Shoreline, WA (US)

(73) Assignee: Animas Corporation, West Chester, PA (US)

( * ) Notice: Subject to any disclaimer, the term of this patent is extended or adjusted under 35 U.S.C. 154(b) by 0 days.

(21) Appl. No.: 10/024,894

(22) Filed: Dec. 18, 2001

(65) Prior Publication Data

US 2002/0077599 A1 Jun. 20, 2002

Related U.S. Application Data

(60) Provisional application No. 60/256,573, filed on Dec. 19, 2000.

(51) Int. Cl.
*A61M 5/32* (2006.01)

(52) U.S. Cl. .................. 604/162; 604/164.12

(58) Field of Classification Search ........... 604/164.01, 604/164.08, 164.09, 164.12, 263, 533, 535, 604/115, 116, 110, 162; 128/DIG. 26
See application file for complete search history.

(56) References Cited

U.S. PATENT DOCUMENTS

| | | | |
|---|---|---|---|
| 4,601,708 A | 7/1986 | Jordan | |
| 4,755,173 A | 7/1988 | Konopka et al. | |
| 4,787,891 A | 11/1988 | Levin et al. | |
| 4,966,589 A * | 10/1990 | Kaufman | 604/174 |
| 4,988,339 A | 1/1991 | Vadher | |
| 4,994,042 A | 2/1991 | Vadher | |
| 5,147,375 A | 9/1992 | Sullivan et al. | |
| 5,176,662 A | 1/1993 | Bartholomew et al. | |
| 5,257,980 A | 11/1993 | Van Antwerp et al. | |
| 5,368,045 A * | 11/1994 | Clement et al. | 600/567 |
| 5,522,803 A | 6/1996 | Teissen-Simony | |
| 5,545,143 A | 8/1996 | Fischell | |
| 5,562,631 A * | 10/1996 | Bogert | 604/192 |
| 5,586,553 A | 12/1996 | Halili et al. | |
| 5,591,188 A | 1/1997 | Waisman | |
| 5,779,665 A | 7/1998 | Mastrototaro et al. | |
| 5,851,197 A | 12/1998 | Marano et al. | |
| 5,868,711 A | 2/1999 | Kramer et al. | |
| 5,957,895 A | 9/1999 | Sage et al. | |
| 5,980,506 A * | 11/1999 | Mathiasen | 604/535 |
| 5,997,507 A * | 12/1999 | Dysarz | 604/161 |
| 6,093,172 A | 7/2000 | Funderburk et al. | |
| 6,293,925 B1 * | 9/2001 | Safabash et al. | 604/136 |
| 6,607,509 B1 | 8/2003 | Bobroff et al. | |
| 2002/0022855 A1 | 2/2002 | Bobroff et al. | |
| 2002/0072720 A1 | 6/2002 | Hague et al. | |
| 2002/0119711 A1 | 8/2002 | VanAntwerp et al. | |
| 2003/0225373 A1 * | 12/2003 | Bobroff et al. | 604/136 |

* cited by examiner

*Primary Examiner*—Nicholas D. Lucchesi
*Assistant Examiner*—Matthew F. DeSanto
(74) *Attorney, Agent, or Firm*—RatnerPrestia

(57) ABSTRACT

A low-profile inserter for an angled infusion set comprises an inserter housing having a bottom wall, a retainer slidably connected to the inserter housing for movement between retracted and extended positions in a direction substantially parallel with the bottom wall, and a base member connected to the inserter housing. The retainer is adapted to releasably receive a cannula assembly, including a cannula connected to a cannula housing. The base member has a lower surface that is adapted to contact a skin outer surface. The lower surface and bottom wall together form an acute angle. With this arrangement, the cannula can be inserted subcutaneously at the acute angle with respect to the skin outer surface.

6 Claims, 7 Drawing Sheets

TRANSCUTANEOUS INSERTER FOR LOW-PROFILE INFUSION SETS

CROSS-REFERENCE TO RELATED APPLICATIONS

This application claims the benefit of U.S. Provisional Application No. 60/256,573 filed on Dec. 19, 2000.

STATEMENT REGARDING FEDERALLY SPONSORED RESEARCH OR DEVELOPMENT

None.

REFERENCE TO A MICROFICHE APPENDIX

None.

BACKGROUND OF THE INVENTION

This invention relates to medical devices, and more particularly to an automatic inserter for installing an angled or low-profile infusion set in the skin of a person to subcutaneously administer medication or other substances beneficial to health.

Frequent or continuous subcutaneous injection of medication such as insulin is often accomplished through the use of an infusion set or injection port which may remain in place for several days. In the case of frequent injections, the infusion set reduces the need to constantly puncture the skin, thereby minimizing the risk of infection and the formation of scar tissue. For continuous subcutaneous delivery of medication through portable insulin pumps or the like, an infusion set is often used to provide a method of temporarily detaching the pump and fluid line for activities such as dressing or bathing. It is also desirable in this instance to detach the fluid line from the pump as close to the injection site as possible, thereby leaving a relatively small component attached to the body which minimizes any interference during dressing, bathing or other activities.

Angled infusion sets, such as disclosed in my copending U.S. Provisional patent application Ser. No. 09/625,245 filed on Jul. 25, 2000, the disclosure of which is herein incorporated by reference, are especially advantageous due to their low profile during use. See also U.S. Pat. No. 5,522,803 issued to Tiessen-Simoney on Jun. 4, 1996. Such devices include a manual inserter with a handle and an introducer needle that attach to a cannula housing. A self-adhesive pad on the bottom surface of the cannula housing secures the housing to the skin of a person. To insert the infusion set, the user grasps the handle with one hand while pinching a fold of skin between the thumb and forefinger of the other hand. The introducer needle together with the outer end of the cannula are then pushed by the user into the fold of skin. The introducer needle is removed from the cannula housing leaving the cannula inserted in the subcutaneous layer. The housing is then adhesively secured to the skin. A tubing connector from an insulin pump can then be connected to the cannula housing to deliver insulin or other substances to the subcutaneous layer.

While this process is relatively straightforward for more experienced persons, it does require manual dexterity. In addition, the cannula may become kinked during an improper installation and impede the flow of insulin, or may be positioned in an improper skin layer. Surrounding tissue may also be damaged during attempts to correctly position the cannula, causing added pain and trauma to a user. Many users prefer to avoid the trauma associated with self-inserting the introducer needle and cannula into their bodies.

Accordingly, it would be desirous to provide an automatic inserter for angled or low-profile infusion sets, thereby assuring the correct placement of the cannula in the subcutaneous layer at the correct angle while minimizing the trauma associated with cannula installation.

BRIEF SUMMARY OF THE INVENTION

According to one aspect of the invention, a low-profile inserter for an angled infusion set comprises an inserter housing having a bottom wall, a retainer slidably connected to the inserter housing for movement between retracted and extended positions in a direction substantially parallel with the bottom wall, and a base member connected to the inserter housing. The retainer is adapted to releasably receive a cannula assembly, including a cannula connected to a cannula housing. The base member has a lower surface that is adapted to contact an outer skin surface. The lower surface and bottom wall together form an acute angle. With this arrangement, the cannula can be inserted subcutaneously at the acute angle with respect to the outer skin surface.

According to a further aspect of the invention, an inserter for an infusion set comprises an inserter housing, and a retainer slidably connected to the inserter housing for movement between retracted and extended positions. The retainer is adapted to releasably receive the cannula assembly. A biasing member is connected between the retainer and the inserter housing for biasing the retainer toward the extended position. A first release lever is pivotally mounted to the inserter housing. The first release lever includes a first end portion that is exposed through the housing for manipulation by an operator and a second end portion for engagement with the retainer to thereby hold the retainer in the retracted position. In this manner, pivotal movement of the first release lever in a first rotational direction causes disengagement of the second end portion and the retainer to thereby release the retainer.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

Figure 1:
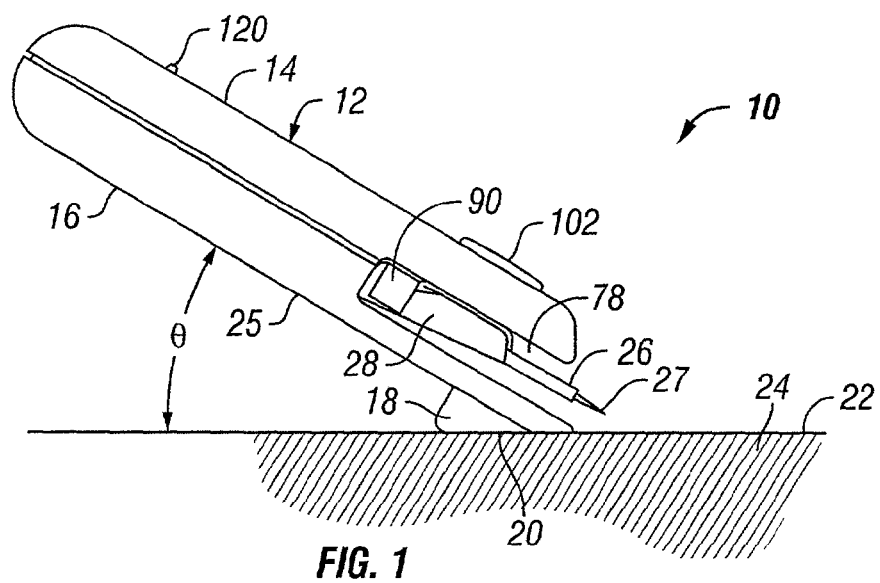
FIG. 1 is a side elevational view of a low-profile inserter assembly according to the invention in a retracted or cocked position.

It is noted that the drawings are intended to represent only typical embodiments of the invention and therefore should not be construed as limiting the scope thereof. The invention will now be described in greater detail with reference to the drawings, wherein like parts throughout the drawing figures are represented by like numerals.

DETAILED DESCRIPTION OF THE INVENTION

Figure 2:
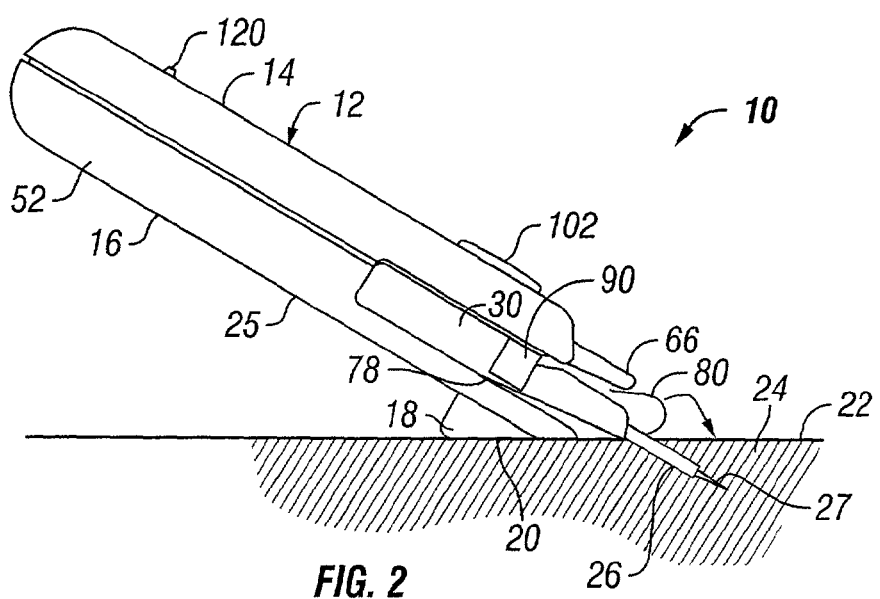
FIG. 2 is a side elevational view of the inserter assembly of FIG. 1 in an extended position with an insertion needle and cannula inserted in the skin (shown in cross section)
Figure 3:
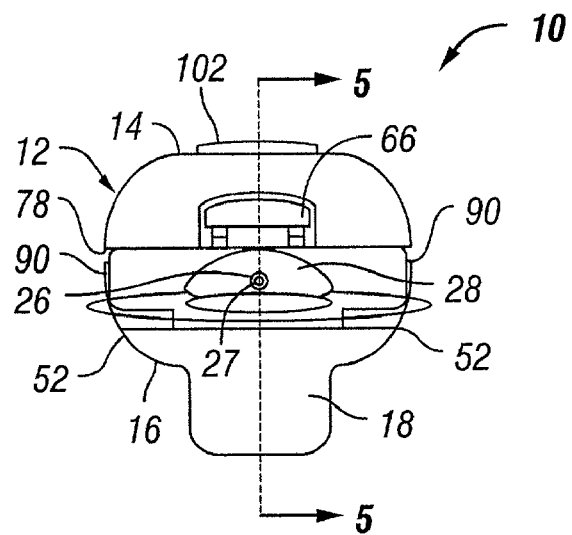
FIG. 3 is a front elevational view of the inserter assembly.

Referring now to the drawings, and to FIGS. 1–3 in particular, a low-profile inserter assembly 10 according to the invention includes a housing 12 with an upper housing portion 14 connected to a lower housing portion 16. An angled alignment guide in the form of a triangular-shaped base 18 is preferably integrally formed with the lower housing portion 16 and includes a lower surface 20 that is adapted to contact an outer surface 22 of skin 24 during use. The lower surface 20 extends at an acute angle θ with respect to a bottom wall 25 of the lower housing portion 16 so that an insertion needle 27 and cannula 26 of a low-profile cannula housing 28 placed in the inserter assembly 10 can be inserted into the skin 24 at the proper angle. The angle θ is in the range of approximately 10° to 40°, and preferably in the range of 15° to 35°, depending on the particular configuration of the cannula housing 28 to be installed. In one preferred embodiment, the angle θ is approximately 30° to accommodate a cannula housing and accompanying cannula that will extend into the subcutaneous layer at approximately 30° with respect to the skin outer surface 22. The housing portions may be constructed of any suitable material, and can be retained together through screws 23 (FIG. 5), interlocking tabs, adhesive, heat-staking, or a combination thereof, or any other well-known fastening means.

Figure 4:
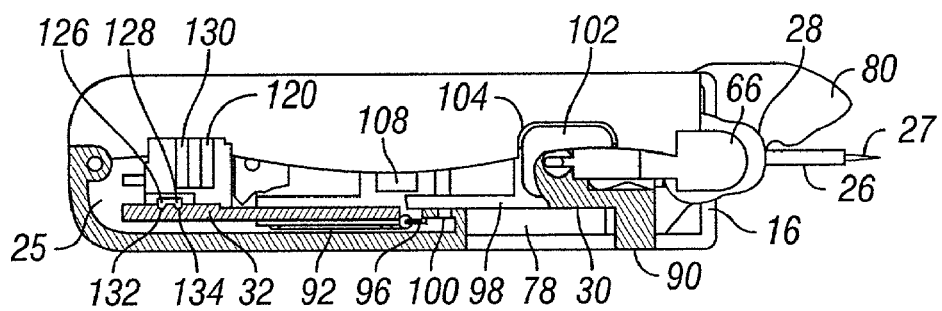
FIG. 4 is top plan view in partial cross section of the inserter assembly.
Figure 6:
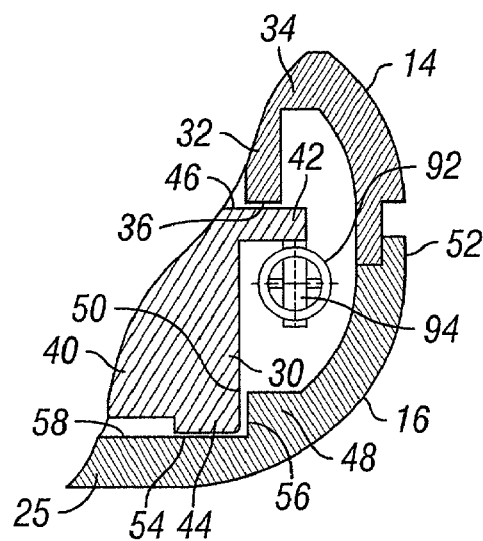
FIG. 6 is an enlarged cross sectional view of a portion of the inserter assembly taken along line 6—6 of FIG. 5.
Figure 5:
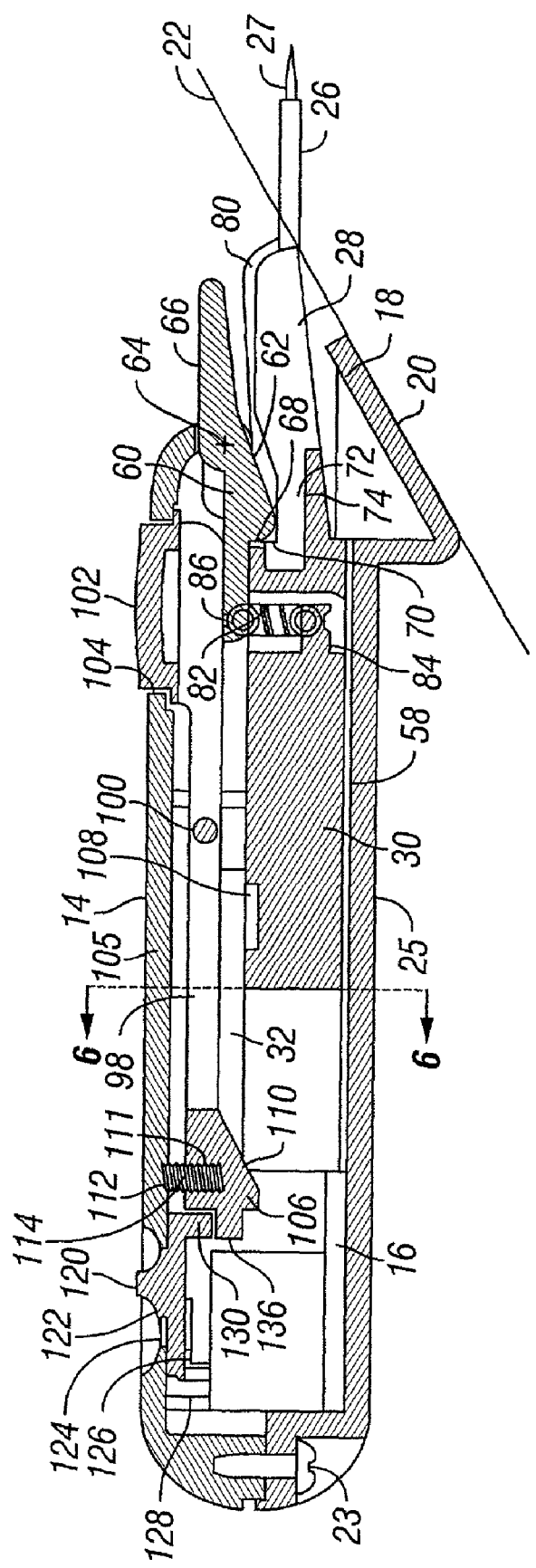
FIG. 5 is an enlarged cross sectional view of the inserter assembly taken along line 5—5 of FIG. 3.

With reference now to FIGS. 4–6, a retainer 30 is slidably mounted in the housing 12 between the upper housing portion 14 and the lower housing portion 16. The retainer 30 includes a main body 40 and a pair of side flanges 42 (only one shown in FIG. 6) that extend laterally from the main body and a pair of bottom flanges 44 (only one shown in FIG. 6) that extend downwardly from the main body. A pair of spaced guide ribs 32 extend downwardly from an upper wall 34 of the upper housing portion 14. Each guide rib 32 includes a lower surface 36 that slidably contacts an upper surface 46 of one of the side flanges 42. A pair of spaced shoulders 48 (only one shown in FIG. 6) are formed at the intersection of the bottom wall 25 and opposite side walls 52 of the lower housing portion 16. Each bottom flange 44 includes a side surface 50 and a lower surface 54 that slidably contact a shoulder side surface 56 and an inner surface 58 of the bottom wall 25, respectively, to guide sliding movement of the retainer 30 in a substantially linear direction between a retracted position (FIG. 1) and an extended position (FIG. 2).

As best shown in FIG. 5, an infusion set release lever 60 is pivotally connected to a forward end of the retainer 30 at a pivot joint 64. The pivot joint 64 may include fingers (not shown) on the lever 60 that extend in opposite directions and fit into opposed depressions (not shown) in the retainer 30. A release button 66 is formed at a forward end of the lever 60 for manipulation by a user. A downwardly-extending catch 68 is formed on the lever 60 rearwardly of the pivot joint 64 and normally seats against a depression 70 in the top of a handle portion 72 of the cannula housing 28. A lower ramped surface 62 extends from the release button 66 to the catch 68 to facilitate connection of the cannula housing 28 to the retainer 30. A slot 74 is formed in the forward end of the retainer 30 for receiving the handle portion 72. A slot 78 (FIG. 4) is also formed in the housing 12 between the upper housing portion 14 and the lower housing portion 16 to accommodate an adhesive-backed mounting pad 80 associated with the cannula housing 28 since, as shown in FIGS. 3 and 4, the pad is wider than the housing 12. In a further embodiment, the housing may be wide enough to completely receive the mounting pad 80, as will be described in further detail below.

The release button 66 is normally biased upwardly by means of a tension spring 82 connected between a forwardly extending hook 84 of the retainer 30 and a rearwardly extending hook 86 of the release lever 60. In this position, the cannula housing 28 is locked to the retainer 30 and is slidable therewith along the housing 12 between the extended and retracted positions. Since the release lever 60 is pivotally connected to the retainer 30, it is also slidable with the retainer to maintain the cannula housing in a locked position until the housing is released by depressing the release button 66. When the retainer 30 is retracted, the release button 66 is located within the housing 12 and therefore cannot be accessed until the retainer is extended to expose the release button. In this manner, the cannula housing 28 cannot be inadvertently released during handling or positioning of the inserter assembly 10, to thereby reduce the possibility of cannula contamination and/or injury. Depression of the release button 66 when the retainer 30 is extended causes the release lever 60 to rotate (clockwise as viewed in FIG. 5) about the pivot joint 64 against bias from the spring 82 until the catch 68 clears the handle portion 72 of the cannula housing 28. In this position, the cannula housing and inserter assembly can be separated.

As shown in FIG. 4, a pair of cocking levers 90 extend in opposite directions from opposite sides of the retainer 30 and into the housing slot 78. The cocking levers 90 can be grasped by a user to move the retainer 30 and attached cannula housing 28 into the retracted position. A pair of tension springs 92 (only one shown in FIGS. 4 and 6) are located on opposite sides of the retainer 30. Each tension spring 92 has one end connected to a hook 94 projecting downwardly from a rear end of the retainer side flange 42 and an opposite end connected to a hook 96 extending from the guide flange 32 of the upper housing portion 14. In this manner, the retainer 30 is normally biased toward the extended position. In an alternative arrangement, a single, centrally mounted tension or compression spring may be used to bias the retainer 30 toward the extended position. In a further embodiment, the one or both tension springs may be replaced with other biasing means, such as an elastomeric member, an air cylinder, and so on.

A retainer release lever 98 (FIG. 5) is pivotally connected to the upper housing portion 14 by a pivot pin 100 that extends between the guide flanges 32 and through the lever 98. A release button 102 is located at a forward end of the release lever 98 and projects upwardly through an opening 104 in an upper wall 105 of the upper housing portion 14. A catch 106 is located at a rearward end of the release lever 98 and projects downwardly therefrom. The catch 106 is arranged to fit within a recess 108 of the retainer 30 and hold the retainer in the retracted position under bias from the tension spring 92. A compression spring 114 is positioned in a bore 110 formed in the rearward end of the release lever 98 and extends to a corresponding depression 112 formed in the upper wall 105 of the upper housing portion 14 to normally bias the catch 106 toward the recess 108.

In order to retract the retainer 30, including the attached cannula housing 12, to a cocked position, the levers 90 (FIG. 4) are grasped by a user to slide the retainer 30 rearwardly in the housing 12. A rear end of the retainer is initially in contact with a lower ramped surface 110 of the catch 106 and rearward movement of the retainer causes the catch 106 to rotate upwardly about the pivot pin 100 (clockwise as viewed in FIG. 5) against bias force from the spring 114 until the catch 106 is clear of the retainer. Further rearward movement of the retainer causes the catch 106 to snap into the recess 108 with a clear audible sound to thereby indicate to a user that the retainer 30 is properly cocked.

Once in the retracted position, the inserter assembly can be placed on the skin of a patient with the lower surface 20 of the base 18 positioned against a user's or patient's outer skin 22. The release button 102 can be depressed to rotate the catch 106 out of the recess 108, which causes the retainer 30 to slide forwardly to the extended position under force from the springs 92 at a relatively rapid rate. Forward movement of the retainer in this manner causes the needle 27 and cannula 26 to pierce the skin at the proper angle and enter into the subcutaneous layer at the proper distance. The cannula housing 28 can then be released from the inserter assembly 10 by depressing the release button 66, as previously described. The mounting pad 80 can then be secured to the skin and the needle 27 removed in a well-known manner, thus leaving the cannula 26 in place.

A safety button 120 is mounted in the upper housing portion 14 between the guide flanges 32 for limited forward and rearward sliding movement. The safety button 120 includes an upper portion 122 that extends through a rear opening 124 in the top wall 105 for grasping by a user. A pair of resilient arms 126 (only one shown in FIG. 4) extend from a lower portion 130 of the button 120. A head 128 is formed at the free end of each arm and is positioned to engage one of two detents 132, 134 formed in the guide flanges 32 which define unlocked and locked positions, respectively, of the safety button 120. In the locked position, the lower portion 130 of the safety button 120 is adjacent a ledge 136 of the catch 106 (FIG. 5), to prevent upward movement of the catch 106 and thus inadvertent release of the retainer 30 and the attached cannula housing 28. In the unlocked position, the ledge 136 is clear of the lower portion 130 to move upwardly when the release button 102 is depressed or when the retainer 30 is moved to the retracted position.

Figure 7:
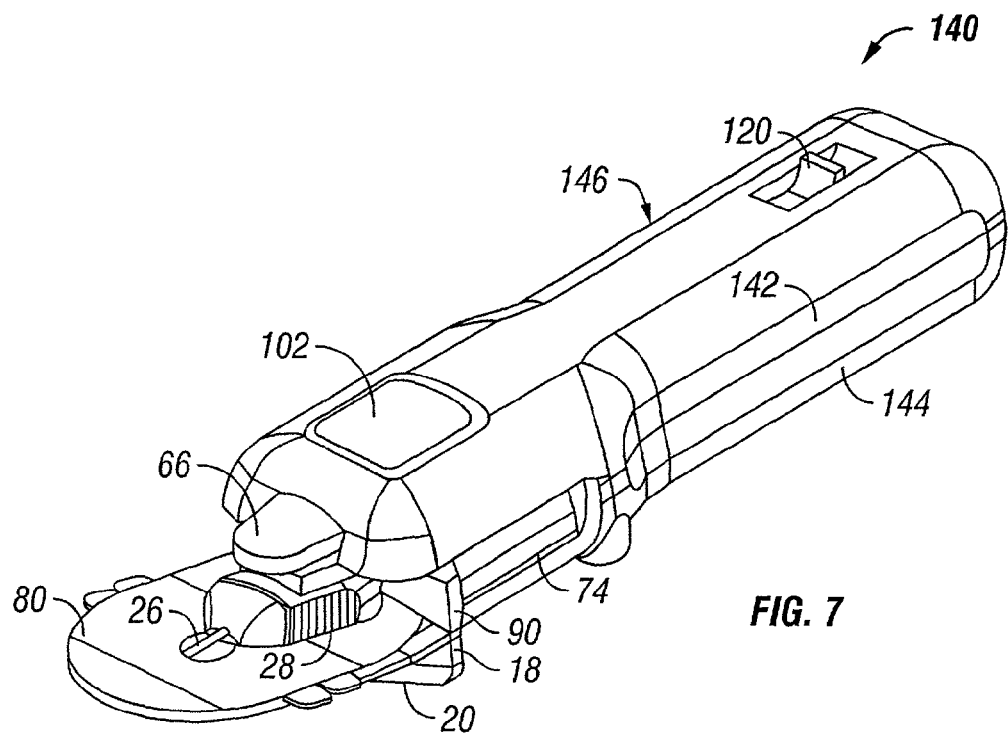
FIG. 7 is an isometric view of a low-profile inserter assembly according to a second embodiment of the invention.
Figure 8:
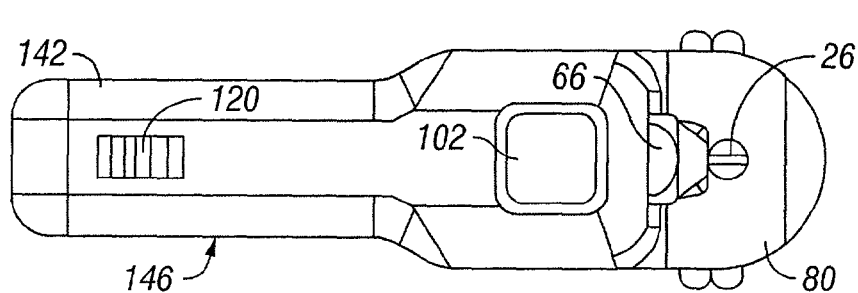
FIG. 8 is a top plan view of the inserter assembly second embodiment.

With reference now to FIGS. 7 and 8, a low-profile inserter assembly 140 according to a second embodiment of the invention is illustrated, wherein like parts in the previous embodiment are represented by like numerals. The inserter assembly 140 is similar in construction to the inserter assembly 10, with the exception that an upper housing portion 142 and lower housing portion 144 are narrowed in width behind the release button 102 to form a narrowed handle portion 146 that is easier to hold and manipulate. This narrower width necessitates moving the tension springs 92 (not shown in FIG. 7) inward, closer to the longitudinal centerline of the housing. These springs will now be located under the retainer 30 rather than on each side as shown in FIGS. 4 and 5. However they are attached to the retainer side flange 42 and guide flange 32 of the upper housing portion 142 in a similar manner.

Figure 9:
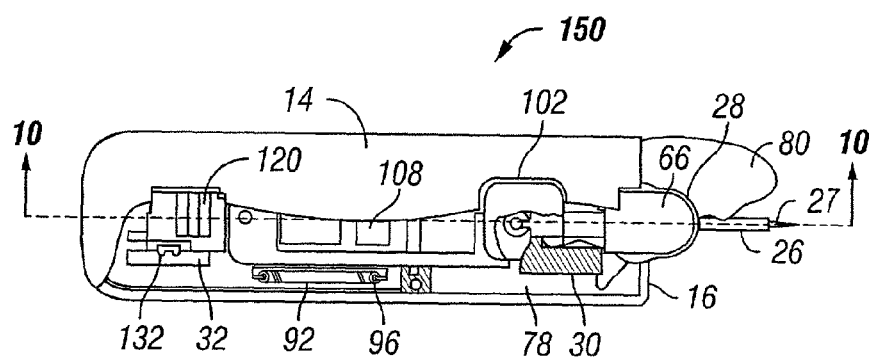
FIG. 9 is top plan view in partial cross section of a low-profile inserter assembly according to a third embodiment of the invention.
Figure 11:
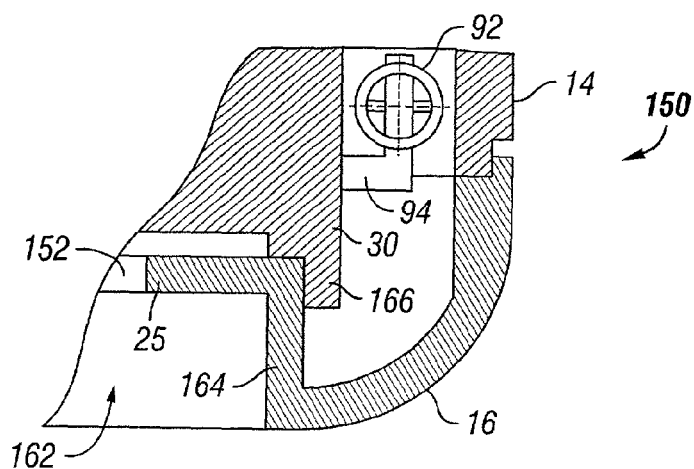
FIG. 11 is an enlarged cross sectional view of a portion of the inserter assembly taken along line 11—11 of FIG. 10.
Figure 10:
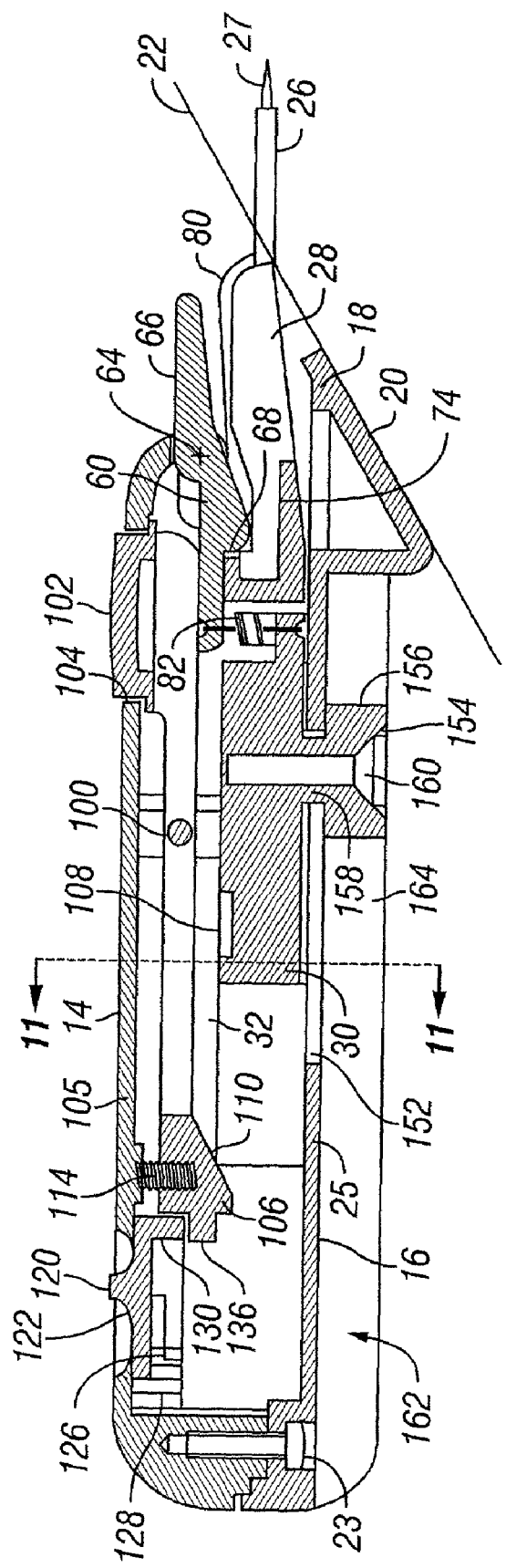
FIG. 10 is an enlarged cross sectional view of the inserter assembly second embodiment taken along line 10—10 of FIG. 9.

With reference now to FIGS. 9–11, a low-profile inserter assembly 150 according to a third embodiment of the invention is illustrated, wherein like parts in the previous embodiments are represented by like numerals. In this embodiment, a slot 152 is formed in the bottom wall 25 of the lower housing portion 16. A single cocking lever 154 extends downwardly through the slot 152 from the retainer 30. As shown, the cocking lever 154 includes a head portion 156 that is larger than the slot and a neck portion 158 that extends through the slot. The neck portion 158 is preferably integrally formed with the retainer 30. A fastener 160 is countersunk in the head portion 156 and extends through the head and neck portions 156, 158 and into the retainer 30 for securing the head portion to the retainer.

The bottom wall 25 is formed in a depression 162 of the lower housing portion 16 and is defined by a pair of inner side walls 164 (only one shown in FIG. 9) that extend downwardly from the bottom wall 25. An L-shaped guide flange 166 is formed at each longitudinal side of the retainer 30 and contacts the bottom wall 25 and inner side wall 164 to guide sliding movement of the retainer in a substantially linear direction.

Operation of the inserter assembly 150 is similar to the operation of the inserter assembly 10, with the exception that a user sets the retainer in a retracted position by pushing the head portion 156 of the cocking lever 154 rearwardly until the catch 106 is located in the recess 108 of the retainer to thereby hold the retainer in the retracted position under bias force from the springs 92. The head portion 156 is preferably entirely located within the depression 162 of the lower housing portion 16 to prevent interference between the head portion and other objects, such as the skin or clothing of a user, and thus possible injury or misplacement of the cannula assembly in the skin during release of the retainer 30.

Figure 12:
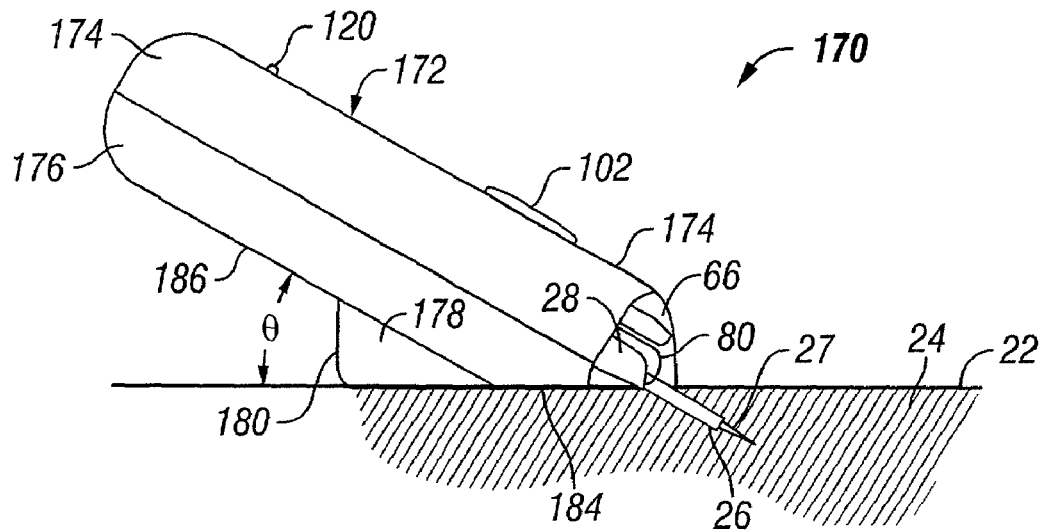
FIG. 12 is a side elevational view of a low-profile inserter assembly according to a fourth embodiment of the invention.
Figure 13:
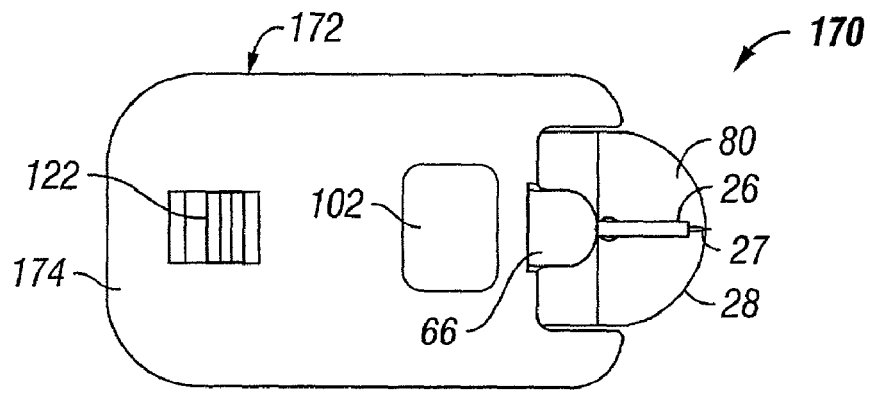
FIG. 13 is a top plan view of the inserter assembly fourth embodiment.
Figure 14:
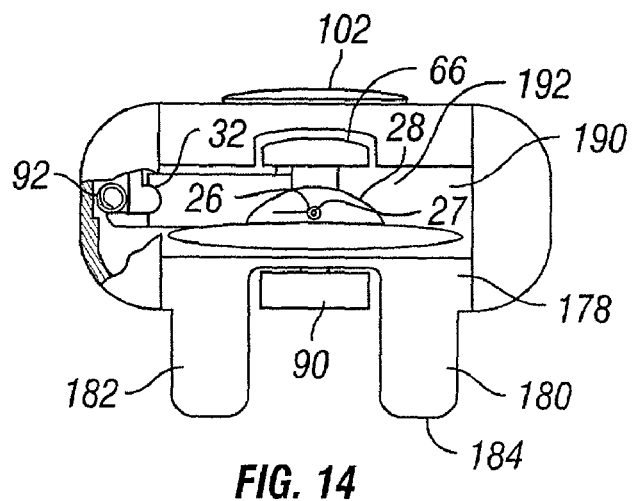
FIG. 14 is a front elevational view in partial cross section of the inserter assembly fourth embodiment.

With reference now to FIGS. 12–14, a low-profile inserter assembly 170 according to a fourth embodiment of the invention is illustrated, wherein like parts in the previous embodiments are represented by like numerals. The inserter assembly 170 includes a housing 172 that is relatively wide in comparison to the previous embodiments. The housing 172 has an upper housing portion 174 connected to a lower housing portion 176 in a manner as previously described. A bifurcated base 178 is preferably integrally formed with the lower housing portion 176 and includes spaced feet 180, 182. Each foot has a lower surface 184 that extends at an acute angle θ with respect to a lower surface 186 of the lower housing portion 176 so that an insertion needle 17 and cannula 26 of a low-profile cannula housing 28 placed in the inserter assembly 170 can be inserted into the skin 24 at the proper angle, as previously described. In one preferred embodiment, the angle θ is approximately 30° to accommodate a cannula that will extend approximately 30° with respect to the outer skin surface 22. However, the actual angle can vary depending on the shape of the cannula housing, as well as the length of the needle and cannula assembly 26. The spaced-apart feet offer greater stability over the previous embodiment and permit a fold of skin to be inserted therebetween during insertion of the needle and cannula assembly 26 into the subcutaneous layer.

A generally vertically extending channel 190 is formed in a forward end of the housing 172. Preferably, the channel is wide enough to receive the cannula housing 28 and the mounting pad 80. A generally horizontally extending slot 192 is formed between the upper housing portion 174 and lower housing portion 176 and intersects with the channel 190. The slot 192 is dimensioned to receive the cannula housing 28, the mounting pad 80, and the release button 66 so that the cannula housing and mounting pad can be releasably connected to the retainer and moved into and out of the housing 172 without obstruction.

It will be understood that the terms relating to orientation and/or position, such as upper, lower, forward, rearward, downward, bottom, and side, including their respective derivatives, as may be used throughout the specification, refer to relative rather than absolute orientations and/or positions.

While the invention has been taught with specific reference to the above-described embodiments, those skilled in the art will recognize that changes can be made in form and detail without departing from the spirit and the scope of the invention. For example, although the present invention has been described for use with a low profile or angled infusion set, it will be understood that the invention may be used to insert straight infusion sets or other types of needles and/or cannulas. Thus, the described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

I claim:

1. An inserter for a low-profile angled infusion set, the low-profile inserter comprising:
   an inserter housing having a bottom wall, and a distal end defining an opening therein;
   a retainer slideably mounted in the inserter housing for movement between retracted and extended positions in a direction substantially parallel with the bottom wall, the retainer being adapted to releasably receive the infusion set, including a cannula and an insertion needle, the cannula and insertion needle defining an insertion axis;
   a tension spring extending between two points for biasing said retainer toward said extended position, said tension spring being movable between an expanded position when said retainer is in said retracted position, and a contracted position when said retainer is in said extended position;
   a first release button for releasing said tension spring from said expanded position, said first release button movable in a direction substantially normal to said insertion axis;
   a second release button for releasing the infusion set from the retainer; and
   a base member connected to the inserter housing, the base member having a lower surface that is adapted to contact a user's skin surface, the lower surface and the bottom wall forming an acute angle, wherein the cannula and the insertion needle are guided to be inserted subcutaneously along the insertion axis at said acute angle with respect to the skin surface.

2. An inserter according to claim 1, and further comprising a safety member slideably mounted to the inserter housing to prevent inadvertent release of the retainer.

3. An inserter according to claim 1, wherein the acute angle is in the range of about 10 degrees to about 40 degrees.

4. An inserter according to claim 1, wherein the acute angle is approximately 30 degrees.

5. An inserter for an infusion set, the inserter comprising:
   an inserter housing defining an opening in a distal end thereof;
   a retainer slideably connected to the inserter housing for movement between retracted and extended positions, the retainer being adapted to releasably receive the infusion set including a cannula and an insertion needle, the cannula and the insertion needle defining an insertion axis;
   a biasing member connected between the retainer and the inserter housing for biasing the retainer toward the extended position, said biasing member being expanded when said retainer is in said retracted position, and contracted when said retainer is in said extended position;
   a first release button for releasing said biasing member from being expanded, movable in a direction substantially normal to said insertion axis;
   a second release button for releasing the infusion set from the retainer; and
   a base attached to a lower surface of said inserter housing defining an acute angle with respect to said inserter housing, for guiding the insertion needle and the cannula to be inserted subcutaneously in skin of a user, along the insertion axis and at the acute angle with respect to the skin.

6. A method for inserting an insertion needle and a cannula into skin of a user, comprising the steps of:
   providing an inserter housing having a bottom wall, a distal end defining an opening therein, and a base member attached to the bottom wall proximate the distal end, said base member including a lower surface adapted to contact the skin and defining an acute angle with said bottom wall;
   slidably mounting a retainer within said inserter housing, movable between a retracted position and an extended position, said extended position being substantially parallel with said bottom wall of said inserter housing;
   mounting the cannula and the insertion needle in said retainer to define an insertion axis;
   providing a tension spring between two points for biasing said retainer toward said extended position, movable between an expanded position and a contracted position;
   releasing said tension spring by pressing a release button proximate said distal end of said inserter housing, in a direction substantially normal to the insertion axis, thereby releasing said spring to move from said expanded position to said contracted position and move said retainer to said extended position, whereby said insertion needle and said cannula are guided to be inserted subcutaneously in the skin at said acute angle with respect to the skin; and
   depressing a second release button to release the cannula and the insertion needle from the retainer.

* * * * *